United States Patent [19]

Abe et al.

[11] 4,425,237
[45] Jan. 10, 1984

[54] METHOD FOR SEPARATING T CELLS FROM LEUKOCYTES

[75] Inventors: Tsutomu Abe; Tsutae Akao; Akihiko Ikeda, all of Fuji, Japan

[73] Assignee: Asahi Kasei Kogyo Kabushiki Kaisha, Osaka, Japan

[21] Appl. No.: 354,402

[22] Filed: Mar. 3, 1982

[30] Foreign Application Priority Data

Mar. 10, 1981 [JP] Japan .................................. 56-33070

[51] Int. Cl.³ ............................................ B01D 15/00
[52] U.S. Cl. ..................................... 210/692; 210/927
[58] Field of Search .............................. 210/692, 927; 260/112 B

[56] References Cited

U.S. PATENT DOCUMENTS

| | | | |
|---|---|---|---|
| 3,794,584 | 2/1974 | Kunin | 210/692 |
| 4,256,588 | 3/1981 | Hoehn et al. | 210/692 |
| 4,257,938 | 3/1981 | Hosoi et al. | 210/927 |

Primary Examiner—Ivars C. Cintins
Attorney, Agent, or Firm—Sprung, Horn, Kramer & Woods

[57] ABSTRACT

The use of a hydrophobic, water-insoluble, granular porous organic polymer having an average pore diameter of 500 to below 5,000Å has been found to be extremely effective for separating T cells from leukocytes when the latter is contacted with the porous organic polymer in the presence of an animal serum protein.

8 Claims, 1 Drawing Figure

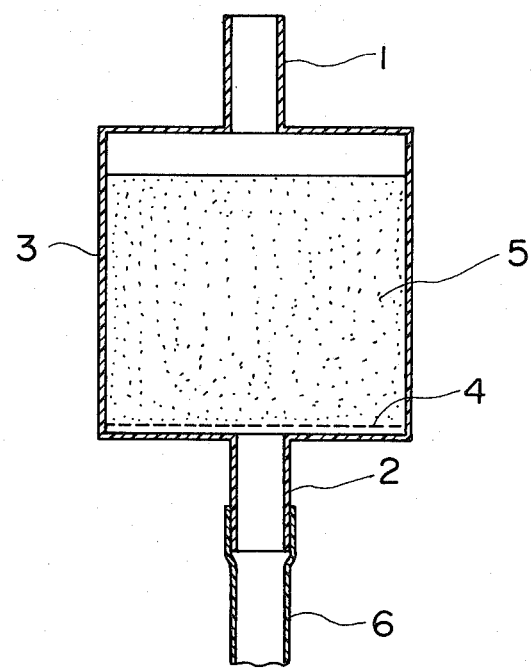

METHOD FOR SEPARATING T CELLS FROM LEUKOCYTES

This invention relates to a novel method for separating T cells from leukocytes. More particularly, the present invention is concerned with a method for separating T cells from leukocytes, which comprises contacting an animal serum protein solution having leukocytes suspended therein with a hydrophobic, water-insoluble, granular porous organic polymer and recovering T cells of the leukocytes in the form of cells unadsorbed on said porous organic polymer.

The term "T cell" as used herein means a certain kind of lymphocyte present in the human body that forms a rosette with a neuraminidase-treated sheep erythrocyte. The non-T cell includes lymphocytes not recognized as a T cell (B cell and Null cell), a monocyte and a granulocyte.

The T cell accounts for 70 to 85% of lymphocytes present in the human peripheral blood. It participates in control of antibody production and various immunological reactions, such as cytotoxic reaction. While the T cell plays important roles as mentioned above, it has heretofore been conceived that it is not feasible to obtain T cells by way of a single separating process. Therefore, intensive efforts have been made in the art to obtain T cells of high purity in high yield while ensuring a high survival rate thereof by the combined use of various separating techniques. Effective separation of T cells is an essential theme in immunology, but known techniques still involve various problems, so that any effective method for separating T cells was not developed.

Heretofore, to obtain T cells from the peripheral blood, a lymphocyte-rich leukocyte suspension, of which the lymphocyte concentration is 70 to 90%, is first fractionated by a specific gravity gradient centrifugation using a hyperdensity liquid such as Ficoll-sodium diatrizoate solution. From the resulting leukocyte suspension, T cells are separated in any of the following manners:

(1) Adding neuraminidase-treated sheep erythrocytes capable of forming rosettes with T cells to the above-mentioned suspension, allowing the mixture to stand still in a cool place for several hours, and again subjecting the mixture to a specific gravity gradient centrifugation;

(2) Contacting the above-mentioned suspension with nylon fibers so that T cells are separated as a fraction unadsorbed on the nylon fibers due to the difference in adsorbability onto the nylon fibers between the T cell and non-T cell, that is, the adsorbability of the former onto the nylon fibers is much lower than that of the latter; and (3) Staining the T cells present in the above-mentioned suspension with a fluorescent dye labeled antiserum capable of recognizing a T cell, and separating the resulting fluorescent cell fraction by means of a fluorescence activated cell sorter.

The first manner described above, however, is accompanied by a serious drawback that the co-presence of a sheep erythrocyte and a lymphocyte leads to stimulation of the lymphocyte. Therefore, the T cells obtained by this manner are not suitable for the purpose of studying the role of the T cell in the immunological system.

According to the second manner described above, a sufficient separation of T cells from non-T cells cannot be achieved, and the yield of T cells of high purity is very low.

The third manner described above is theoretically to provide T cells of the highest purity. However, it is accompanied by several drawbacks. One of such drawbacks is that the cells undergo stimulus or lesion due to the use of an antiserum. Another is that it is difficult to obtain as many lymphocytes as $10^7$ to $10^8$ since this manner inevitably involves the step of isolating cells one by one.

Taking into consideration the above-described current situation of T cell separating methods, we have made intensive studies on adsorption phenomena of T cells and non-T cells on foreign matter surfaces with a view to obtaining T cells of high purity in high yield without exerting any immunostimulus thereon. As a result, we have found that a water-insoluble, hydrophobic, granular porous organic polymer having coarse surfaces, namely having an average pore diameter of 500 Å to below 5,000 Å, is a suitable material for separating T cells from a leukocyte suspension. Based on this finding, we have completed this invention.

It is, therefore, an object of the present invention to provide a method of efficiently separating high-purity T cells from a leukocyte suspension in high yield, utilizing a material of the kind described above.

The foregoing and other objects, features and advantages of the present invention will be apparent to those skilled in the art from the following detailed description and appended claims taken in connection with the accompanying drawing in which:

FIGURE shows a diagrammatic cross-sectional view of an apparatus to be employed for practicing the method of the present invention.

According to the present invention, there is provided a method for separating T cells from leukocytes which comprises contacting an animal serum protein solution having leukocytes suspended therein, said leukocytes comprising T cells and non-T cells, with a hydrophobic, water-insoluble, granular porous organic polymer having an average pore diameter of 500 Å to below 5,000 Å to adsorb the non-T cells on said porous organic polymer while leaving substantially the T cells unadsorbed, and recovering the T cells left unadsorbed.

The T cell and non-T cell exhibit markedly different adsorbabilities onto the porous organic polymer to be employed in the present invention. Therefore, it is possible to obtain T cells efficiently as a fraction not adsorbed on said porous polymer by contacting a leukocyte suspension with said material in the presence of animal serum protein as will be explained later in more detail.

The term "leukocyte suspension" as used herein means a mixture in which leukocytes, viz. granulocytes, lymphocytes and monocytes, are floating together with erythrocytes of which the amount does not exceed 10 times that of the leukocytes. The leukocyte suspension may be prepared by centrifugation, specific gravity gradient centrifugation using a Ficoll-sodium diatrizoate solution or the like, or by a dextran precipitation method. The leukocyte suspension to be employed in the method of the present invention generally contains leukocytes in an amount of $1 \times 10^3$ to $2 \times 10^7$/ml.

The purposes of the present invention cannot be fully attained even by utilizing a hydrophobic organic polymer if the polymer has smooth surfaces. The purposes of the present invention can be attained only by utilizing a hydrophobic, water-insoluble and granular porous organic polymer having an average pore diameter of 500 Å to below 5,000 Å, preferably 600 Å to below 3,500 Å, more preferably 1,000 Å to below 2,500 Å.

The average pore diameter as used herein is measured using a mercury penetration porosimeter. More specifically, mercury is forced, under increasing pressure, into pores of a porous material to be measured and the pore volume is determined from the amount of mercury occluded in pores of the sample, and the pore diameter is calculated based on the principle that the diameter of a pore is in inverse proportion to the pressure necessary for forcing mercury into the pores. This measurement method is detailed in Chapter 10 of "Fine Particle Measurement" written by Clyde Orr, Jr. and J. M. Dallavalle and published by the Macmillan Company, New York in 1959. According to this method, even pores having a pore diameter as small as 35°–40 Å can be measured. In the present invention, the term "pore" is intended to mean an open pore communicated to the outside surface of the polymer and having a pore diameter of at least 40 Å, and the pore volume is determined with respect to such open pores. To determine the "average pore diameter", $dV/d\log r$ is plotted against $\log r$ wherein r represents the pore diameter and V denotes the cumulative pore volume measured by the mercury penetration porosimeter on a semilogarithmic coordinate paper to obtain a pore size distribution curve. The figure generated by the log r axis and the above obtained curve is divided into two equal parts by a line perpendicular to the log r axis. The diameter corresponding to the intersecting point obtained by the log r axis and the line dividing the figure is regarded as the average pore diameter.

When the average pore diameter is below 500 Å, the intended coarse surfaces cannot be obtained, thereby causing the adsorption of non-T cells on the separating material to be insufficient. When the average pore diameter is above 5,000 Å, T cells also tend to be adsorbed on the separating material, thereby causing separation of T cells to be difficult.

It is needed that the organic polymer used as a T cell separating material according to the present invention is hydrophobic and water insoluble. As the suitable hydrophobic and water insoluble polymers, there can be mentioned, for example, polymers and copolymers of ethylene, propylene, vinyl chloride, vinyl acetate, styrene, divinylbenzene and/or methyl methacrylate, nylon, polycarbonate, polyethylene terephthalate and polyester copolymers. The term "hydrophobic polymer" as used herein means a polymer having a solubility parameter ($\delta$) defined by Hildebrand (see J. H. Hildebrand and R. L. Scott, "The Solubility of Non-Electrolytes," Dover, New York, 1964) of 0 to 12. The hydrophobic organic polymer has the inherent property of capturing leukocytes, and it realizes effective separation of T cells in the presence of animal serum protein.

The separating material used according to the present invention may be prepared according to any of the customary polymerization methods. However, it is preferred that a porous copolymer of a monovinyl monomer, such as styrene, and a crosslinkable monomer, such as divinylbenzene, be employed, because a combination of such monomers enables free control of the porosity of a polymer during the polymerization step thereof.

The kind of the monovinyl monomer to be employed for the preparation of the porous polymer is not critical. As the suitable monovinyl monomer, there can be mentioned, for example, hydrocarbons, such as styrene, methylstyrene, diphenylethylene, ethylstyrene, dimethylstyrene, vinylnaphthalene, vinylphenanthrene, vinylmesitylene, 3,4,6-trimethylstyrene, 1-vinyl-2-ethylacetylene; styrene derivatives, such as chlorostyrene, methoxystyrene, bromostyrene, cyanostyrene, fluorostyrene, dichlorostyrene, chloromethylstyrene, trifluorostyrene, trifluoromethylstyrene, N,N-dimethylaminostyrene, nitrostyrene and aminostyrene; vinyl sulfides, such as methyl vinyl sulfide and phenyl vinyl sulfide; acrylonitriles, such as acrylonitrile, methacrylonitrile, and α-acetoxyacrylonitrile; acrylic acid, methacrylic acid; acrylates, such as methyl acrylate, lauryl acrylate, chloromethyl acrylate and ethyl acetoxylacrylate; methacrylates, such as cyclohexyl methacrylate, dimethylaminoethyl methacrylate, glusidyl methacrylate, tetrahydrofurfuryl methacrylate and hydroxyethyl methacrylate; diethyl maleate, diethyl fumarate; vinyl ketones, such as methyl vinyl ketone and ethyl isopropenyl ketone; vinylidene compounds, such as vinylidene chloride, vinylidene bromide and vinylidene cyanide; acrylamides, such as acrylamide, methacrylamide, N-phenylacrylamide, N-butoxymethacrylamide, diacetonacrylamide and N,N-dimethylaminoethylacrylamide; esters of vinyl alcohol and aliphatic acid, such as vinyl acetate, vinyl butyrate and vinyl caprylate; thioesters, such as phenyl thiomethacrylate, methyl thioacrylate and vinyl thioacetate; and heterocyclic vinyl compounds, such as N-vinylsuccinimide, N-vinylpyrrolidone, N-vinylphthalimide, N-vinylcarbazole, vinylfuran, 2-vinylbenzofuran, vinylthiophene, vinylimidazole, methylvinylimidazole, vinylpyrazole, vinyl oxazolidone, vinylthiazole, vinyltetrazole, vinylpyridine, methylvinylpyridine, 2,4-dimethyl-6-vinyltriazine and vinylquinoline.

As the crosslinkable monomer to be employed for the preparation of the porous polymer, there can be mentioned, for example, divinylbenzene, divinyltoluene, divinylxylene, divinylnaphthalene, divinylethylbenzene, trivinylbenzene, divinyldiphenyl, divinyldiphenylmethane, divinyldibenzyl, divinylphenyl ether, divinyldiphenylsulfide, divinyldiphenylamine, divinyl sulfone, divinyl ketone, divinylfuran, divinylpyridine, divinylquinoline, di(vinylpyridinoethyl)ethylenediamine, diallyl phthalate, diallyl maleate, diallyl fumarate, diallyl succinate, diallyl carbonate, diallyl oxalate, diallyl adipate, dially sebacate, diallyl tartrate, diallylamine, triallylamine, triallyl phosphate, triallyl tricarballylate, triallyl aconitate, triallyl citrate, N,N'-ethylenediacrylamide, N,N'-methylenediacrylamide, N,N'-methylenedimethylacrylamide, ethylene glycol dimethacrylate, triethylene glycol dimethacrylate, polyethylene glycol dimethacrylate, trimethylolpropane trimethacrylate, pentaerythritol tetramethacrylate, 1,3-butylene glycol diacrylate, 1,6-hexanediol diacrylate, trimethylol propane triacrylate, pentaerythritol tetraacrylate, triallyl isocyanurate, 1,3,5-triacryloylhexahydro-1,3,5-triazine and diallylmelamine.

The shape of the separating material to be employed according to the present invention is needed to be granular, preferably spherical, more preferably authenically spherical, in order to increase the separating efficiency thereof for T cells. It is preferred that the grain diameter of the separating material be in the range of 40μ to below 800μ, preferably 40μ to below 350μ. When the grain diameter is below 40μ, the tendency of T cells being adsorbed on the separating material disadvantageously increases. When the grain diameter of the material is 800μ or more, the probability of contact of cells with the material decreases so that more leukocytes flow out without undergoing separation.

The total pore volume of the separating material to be employed in the method of the present invention is measured using a mercury penetration porosimeter as in determining the above-mentioned average pore diameter. It is preferred that the total pore volume be in the range of 0.1 to below 4.0 ml/g, preferably 0.3 to below 3.0 ml/g. When the total pore volume is below 0.1 ml/g, non-T cells in a leukocyte suspension cannot be sufficiently adsorbed on the separating material as in the case of a polymer with smooth surfaces, thereby causing practical separation of T cells by the material to be impossible. When the total pore volume is 4.0 ml/g or more, the material is poor in mechanical strength, thereby causing the porous structure of the material to be collapsed so that the separating material cannot be practically used.

It is preferred that the porous organic polymer to be employed according to the present invention carry an acid functional group, because the acid functional group has an effect of preventing T cells from being adsorbed on the separating material. The kind of the acid functional group is not critical. As the suitable acid functional group, there can be mentioned, for example, a sulfonic acid group, a carboxylic acid group, a phosphonic acid group and a phenol group. The acid functional group may be incorporated into the monomer before polymerization. Alternatively, it may be incorporated into the polymer after polymerization by way of substitution or addition reaction.

It is preferred that the exchange capacity of the acid functional group incorporated in the polymer be 0.1 or less meq/ml. When the exchange capacity exceeds 0.1 meq/ml, the acid functional group tends also to prevent non-T cells from being adsorbed on the separating material, thereby causing the purity of the T cell fraction to be decreased.

A leukocyte suspension to be employed in the present invention may be prepared from a leukocyte layer obtained by ordinary centrifugation. Alternatively, it may be prepared from a lymphocyte-rich layer obtained by a specific gravity gradient centrifugation method. It is preferred in practice that a leukocyte suspension be prepared from a lymphocyte-rich layer obtained by a specific gravity gradient centrifugation method using a hyperdensity liquid, such as Ficoll-sodium diatrizoate solution, because mingling of granulocytes into the suspension is minimized.

In practicing the method of the present invention, an animal serum protein solution having leukocytes suspended therein, in which the concentration of animal serum protein is in the range of 1 to 7 g/dl, is contacted with the separating material. As the suitable animal serum protein solution, there can be mentioned a culture medium or isotonic buffer containing 30% or more of autoserum or fetal mammalian serum and more preferably, 100% purity fetal mammalian serum per se. As the suitable fetal mammalian serum protein, there can be mentioned, for example, those of an equine, a bovine, a sheep, a goat, a mouse, a guinea pig and a human being. When the concentration of animal serum protein is below 1 g/dl, the adsorption of T cells on the separating material disadvantageously increases. The upper limit of the concentration of animal serum protein, namely, 7 g/dl is a value which is self-controlled in view of the maximum concentration of animal serum protein. In the case of a separating material of polymer grains having a diameter as small as 40 to below 75μ, it is preferred that a culture medium or isotonic buffer containing animal serum protein in a concentration of 2.0 g/dl or more be contacted with said material in order to suppress the adsorption of T cells on said material which tends to occur when a small-grain-size separating material is used.

The mechanism of separating T cells according to the present invention has not yet been fully elucidated, but it is believed that the use of a hydrophobic, water-insoluble, granular porous organic polymer having coarse surfaces contributes to effective realization of distinct difference in adsorbability thereto between different cells, whereby substantially all the T cells are separated as a fraction not adsorbed on the porous polymer used in the present invention. To attain effective separation of T cells utilizing the above-mentioned porous polymer, various investigations have been made on the grain diameter of the porous organic polymer, the kind of protein to be co-present and other factors and, as a result, the present invention has been completed.

Turning now to FIGURE, an apparatus to be suitably used for separating T cells according to the present invention comprises an column 3 having an inlet 1 for pouring thereinto a leukocyte suspension and a washing fluid and an outlet 2 for discharging the leukocyte suspension and the washing fluid therefrom, which column 3 is packed with a separating material 5. In the column 3 at a portion before the outlet 2, there is provided a filter 4 having a pore size through which the separating material does not flow out. Another filter (not shown) may be provided in the column at a portion adjacent to the inlet 1. A silicone rubber tube 6 is fitted over the outlet 2 so that the channel for the liquid may be optionally closed or opened by means of a pinch cock (not shown). The kind of the material of the column 3 is not critical as long as it is water-insoluble and provides smooth surfaces of contact with the liquid to be passed through the column. As the suitable material of the column 3, there can be mentioned, for example, polyethylene, polypropylene, polyvinyl chloride, polystyrene, polymethyl methacrylate, nylon, polycarbonate, polyethylene terephthalate and glass. The kind of the material of the filter 4 is not critical as long as it is water-insoluble and provides smooth surfaces of contact with the liquid to be passed through the column. Various materials as set forth above with respect to the column construction can also be used as a material for making the filter. The filter may be attached to the inner wall of the column by any of means capable of not only ensuring secure fixing of the filter but also preventing liquid leakage, such as cement adhesive, hot melt adhesive and screws.

To separate T cells from leukocytes using an apparatus as described above, leukocytes separated from blood by centrifugation or specific gravity gradient centrifugation are rendered floating in a solution containing 1 to 7 g/dl animal serum protein. The resulting mixture is poured into the apparatus which has previously been washed with a solution containing 1 to 7 g/dl animal serum protein to equilibrate the porous organic polymer with the solution. When the mixture has wetted out the separating material, the flowing of the mixture is stopped. The column is then allowed to stand still for a predetermined period of time, usually 30 to 60 minutes, to effect complete adsorption of non-T cells on the separating material while leaving most of T cells unadsorbed. Thereafter, a washing fluid such as a phosphate buffered saline or suitable medium is poured into the column to wash out the cells, mainly T cells, which have been left unadsorbed. It is advantageous that the phosphate buffered saline or medium to be used as a washing fluid contain animal serum protein in a concentration of 0.1 to 7 g/dl. The separation of T cells on the separating material may be conducted at any temperature not causing lesion to the cells, preferably room temperature to 37° C.

Alternatively, it is possible to use as a T cell separating material a hydrophobic, water-insoluble, granular porous organic polymer having an average pore diameter of 500 Å to below 5,000 Å which has animal serum protein adsorbed thereon and dried. When this material is used, it is possible to effect separation of T cells at a decreased concentration of animal serum protein in the solution having leukocytes suspended therein. As the animal serum protein solution to be employed in the method of the present invention, there can be mentioned a medium or buffer of autoserum or fetal mammalian serum having a protein concentration of 1.7 to 7 g/dl, preferably a medium or buffer of fetal mammalian serum having a protein concentration of 2.5 to 7 g/dl and, more preferably, 100% purity fetal mammalian serum per se.

To adsorb animal serum protein on a porous organic polymer to be employed in the method of the present invention, the polymer is first soaked in an animal serum protein solution for 1 to 48 hours, preferably 10 to 48 hours. Then, the mixture is subjected to suction filtration to remove the solution, and the polymer is freeze-dried. The soaking of the polymer may be performed at any temperature not causing deterioration of the animal serum protein, usually 4° to 25° C.

The grain diameter of the separating material having animal serum protein adsorbed thereon and dried may be in the range of 40 to below 800μ. However it is preferred that the grain diameter of such material be in the range of 40 to below 200μ, more advantageously 40 to below 75μ.

When the separating material having animal serum protein adsorbed thereon and dried is used, washing of the apparatus before pouring into the column of the apparatus an animal serum protein solution having leukocytes suspended therein may be performed with the use of a medium or buffer of animal serum having a protein concentration of 0.1 to 7 g/dl. Illustratively stated, the washing to equilibrate the porous organic polymer in the apparatus with a medium or buffer may be performed at lower protein concentrations of the medium or buffer than those employed when the material not having animal serum protein adsorbed thereon is used.

The T cells separated according to the method of the present invention exhibit the same survival rate, blast transformation potential and antibody production control as exhibited by those not subjected to the separation process of the present invention.

The present invention will be illustrated in more detail with reference to the following Examples, which should not be construed to be limiting the scope of the present invention.

EXAMPLE 1

[Preparation of T cell separating material]

A 3-liter three-necked flask equipped with a reflux condenser, a stainless steel-made two-blade stirrer and a thermometer was charged with 100 g of divinylbenzene (having a purity of 56% and containing 44% of vinylethylbenzene as an impurity; hereinafter referred to as "56% divinylbenzene"), 150 g of dimethyl phthalate and 1 g of azobisisobutyronitrile, followed stirring to obtain a homogeneous solution. Then, 1500 g of distilled water containing, dissolved therein, 1.5 g of partially saponified polyvinyl acetate (having a viscosity of 23 cps as measured at 20° C. with respect to a 2% aqueous solution thereof and a degree of saponification of 88%) and 60 g of sodium chloride was added to the above solution, and the mixture was heated at 60° C. for 1 hour, at 70° C. for 2 hours, at 80° C. for 2 hours and at 90° C. for 4 hours while the mixture was agitated at 250 rpm.

The resulting copolymer was found to have a good spherical shape, and the grain diameters were distributed in the range of from 30 to below 100μ. The average pore diameter as measured by a mercury penetration porosimeter was 1400 Å and the total pore volume as measured by a mercury penetration porosimeter was 1.1 ml/g. This copolymer was used as a T cell separating material.

[Preparation of T cell separating apparatus]

The above-obtained copolymer was subjected to wet classification using a stainless steel-made sieve to obtain 2 ml of the separating material having a grain diameter in the range of from 150 to below 350μ. After 2 ml of the separating material thus obtained was sufficiently immersed in phosphate buffered saline (hereinafter referred to as "PBS") and washed with PBS, the separating material was packed into an acrylic resin-made column having an inner diameter of 10 mm and having a filter of nylon net (30μ) in the bottom of the column, an inlet for liquid and an outlet for liquid (see FIG. 1) to obtain a T cell separating apparatus. The T cell separating material was carefully packed into the column not to occlude airpockets in the column.

[Preparation of sample and separation procedures]

A leukocyte fraction [ratio of cells; T cell: 64.9%, B cell: 10.1%, monocyte and granulocyte: 17.8%, remaining cell not elucidated: 7.2% (survival rate of all cells; 98%)] was separated from heparinized human peripheral blood using Ficoll-sodium diatrizoate solution [specific gravity: 1.077 (at 20° C.)] by specific gravity gradient centrifugation and washed with PBS. A leukocyte suspension having a leukocyte concentration of $4 \times 10^6$/ml was prepared by suspending the above-obtained leukocyte fraction in pure fetal calf serum (having a protein content of 4.3 g/dl). 0.5 ml of the leukocyte suspension thus obtained was supplied gently to the inlet of the above-obtained T cell separating apparatus which had previously been washed with 4 ml of pure fetal calf serum. After the suspension sufficiently permeated into the whole separating material, the outlet of the column was closed by pressing the silicon rubber tube using a pinchcock so as to prevent the suspension from flowing out. Then, the column was maintained at 37° C. for 1 hour. Then, the outlet was opened and 4 ml of PBS was added to the inlet of the column, so that the cells which were not adsorbed on the T cell separating material were washed out and the fraction containing the T cells was collected at a flow rate caused by gravity-dropping.

[Analysis of lymphocyte]

The above-obtained fraction containing T cells was analyzed in the following manners.

(1) The recovery of all cells was measured by means of an automatic blood cell counter or by microscopic observation using a hemocytometer.

(2) The number of T cells was determined by the rosette technique utilizing the phenomenon that T cells form rosettes with neuraminidase-treated sheep erythrocytes.

(3) The number of B cells (a kind of non-T cell) was determined by the fluorescent antibody method in which B cells are detected as surface immunoglobulin positive cells.

(4) The total number of both monocytes and granulocytes was determined by the intracellular peroxidase activity detection method.

(5) The survival rate of all cells was determined by the dye exclusion test using trypan blue.

The results are shown in Table 1.

EXAMPLE 2

A copolymer having a good spherical shape was prepared in substantially the same manner as in Example 1 except that 300 g of toluene was added instead of 150 g of dimethyl phthalate. It was found that the grain diameters were distributed in the range of from 30 to below 1000$\mu$. The average pore diameter as measured by a mercury penetration porosimeter was 2300 Å and the total pore volume as measured by a mercury penetration porosimeter was 2.9 ml/g.

The above-obtained copolymer was subjected to wet classification in substantially the same manner as in Example 1 to obtain a T cell separating material having a grain diameter in the range of from 100 to below 300$\mu$. A T cell separating apparatus was prepared in substantially the same manner as in Example 1 except that the above-obtained T cell separating material was used instead of the T cell separating material as obtained in Example 1.

The same leukocyte suspension as prepared in Example 1 was subjected to the same separation procedures as in Example 1 except that the above-obtained T cell separating apparatus was used instead of the T cell separating apparatus as used in Example 1.

The collected fraction containing T cells was analyzed in the same manner as in Example 1. The results are shown in Table 1.

EXAMPLE 3

A copolymer having a good spherical shape was prepared in substantially the same manner as in Example 1 except that 150 g of dioctyl adipate was added instead of 150 g of dimethyl phthalate. It was found that the grain diameters were distributed in the range of from 30 to below 500$\mu$. The average pore diameter as measured by a mercury penetration porosimeter was 1100 Å and the total pore volume as measured by a mercury penetration porosimeter was 1.7 ml/g.

The above-obtained copolymer was subjected to wet classification in substantially the same manner as in Example 1 to obtain a T cell separating material having a grain diameter in the range of from 40 to below 75$\mu$.

A T cell separating apparatus was prepared in substantially the same manner as in Example 1 except that the above-obtained T cell separating material was used instead of the T cell separating material as obtained in Example 1.

The same leukocyte suspension as prepared in Example 1 was subjected to the same separation procedures as in Example 1 except that the above-obtained T cell separating apparatus was used instead of the T cell separating apparatus as used in Example 1, and that a solution consisting of 10% by volume of fetal calf serum (having a protein content of 3.4 g/dl) and 90% by volume of PBS was used, instead of PBS, to wash out the T cells left unadsorbed.

The collected fraction containing T cells was analyzed in the same manner as in Example 1. The results are shown in Table 1.

EXAMPLE 4

The copolymer obtained in Example 1 was subjected to sulfonation using chlorosulfonic acid. The resulting copolymer had an exchange capacity of 0.05 meq/1 ml (wet copolymer).

The above-obtained copolymer was subjected to wet classification in substantially the same manner as in Example 1 to obtain a separating material having a grain diameter in the range of from 40 to below 75$\mu$. The separating material thus obtained was packed in the same column as used in Example 1 to obtain a T cell separating apparatus. After the separating material packed in the column was washed with PBS, 4 ml of pure fetal calf serum (having a protein content of 4.3 g/dl) was added to the column. Then, the separating material packed in the column was left overnight at room temperature, followed by washing with PBS.

The same leukocyte suspension as prepared in Example 1 was added gently to the inlet of the separating apparatus. The subsequent T cell separation procedures were conducted in substantially the same manner as in Example 1.

The collected fraction containing T cells was analyzed in the same manner as in Example 1. The results are shown in Table 1.

EXAMPLE 5

[Preparation of separating material]

The copolymer obtained in Example 1 was subjected to wet classification using a stainless steel-made sieve to obtain a copolymer having a grain diameter in the range of from 40 to below 75$\mu$. After the copolymer thus obtained was sufficiently immersed in PBS and washed with PBS, it was filtered with suction. Then, the copolymer was sufficiently immersed in pure fetal calf serum (having a protein content of 3.4 g/dl) for 12 hours at room temperature (about 23° C.). The excess fetal calf serum adsorbed on the copolymer was removed by suction filtration, and then, the copolymer was freeze-dried to obtain a T cell separating material.

[Preparation of separating apparatus]

2 ml of the above-obtained separating material with fetal calf serum protein had been adsorbed thereon and freeze-dried was packed into the same column as used in Example 1 to obtain a separating apparatus. Then, a solution consisting of 10% by volume of fetal calf serum and 90% by volume of PBS was poured into the column so that the T cell separating material was sufficiently wetted with the solution.

[Preparation of sample and separation procedures]

A leukocyte suspension having a leukocyte concentration of $4 \times 10^6$/ml was prepared by suspending the leukocyte fraction as prepared in Example 1 in a solution consisting of 10% by volume of fetal calf serum having a protein content of 3.4 g/dl and 90% by volume of PBS. 0.5 ml of the leukocyte suspension thus obtained was supplied gently to the inlet of the above-obtained separating apparatus. After the suspension sufficiently permeated into the whole separating material, the outlet of the separating apparatus was closed by pressing the silicon rubber tube using a pinch-cock so as to prevent the suspension from flowing out. Then, the separating apparatus was maintained at 37° C. for 1 hour. The outlet was opened and 4 ml of PBS was added to the inlet of the separating apparatus, so that the cells which were not adsorbed on the separating material were washed out and the fraction containing the T cells was collected at a flow rate caused by gravity-dropping.

The collected fraction containing T cells was analyzed in the same manner as in Example 1. The results are shown in Table 1.

EXAMPLE 6 the copolymer as prepared in Example 2 was subjected to wet classification using a stainless steel-made sieve to obtain a copolymer having a grain diameter in the range of from 75 to below 200μ. Substantially the same procedures as in Example 5 were repeated to obtain a separating material except that the above-obtained copolymer was used instead of the copolymer as used in Example 5 and that a solution consisting of 25% by volume of PBS and 75% by volume of fetal calf serum and having a protein content of 2.5 g/dl originating from the fetal calf serum was used instead of pure fetal calf serum having a protein content of 3.4 g/dl.

Using the above-obtained separating material, a separating apparatus was prepared in substantially the same manner as in Example 5. Then, a solution consisting of 10% by volume of fetal calf serum and 90% by volume of PBS was poured into the column so that the T cell separating material was sufficiently wetted with the solution.

The same leukocyte suspension as prepared in Example 5 was subjected to the same separation procedures as in Example 5 except that the above-obtained T cell separating apparatus was used instead of the T cell separating apparatus as used in Example 5.

The collected fraction containing T cells was analyzed in the same manner as in Example 1. The results are shown in Table 1.

EXAMPLE 7

A leukocyte suspension was prepared in substantially the same manner as in Example 1 except that a PBS solution having a bovine serum albumin dissolved therein in a concentration of 5 g/dl was used instead of pure fetal calf serum.

Using the same separating apparatus as in Exaple 1, the above-obtained leukocyte suspension was subjected to substantially the same separation procedures as in Example 1 except that the T cell separating apparatus was washed with a PBS solution having a bovine serum albumin dissolved therein in a concentration of 5 g/dl instead of pure fetal calf serum prior to use.

The collected fraction containing T cells was analyzed in the same manner as in Example 1. The results are shown in Table 1.

EXAMPLE 8

The copolymer as prepared in Example 2 was subjected to wet classification using a stainless steel-made sieve to obtain a copolymer having a grain diameter in the range of from 400 to below 800μ. The obtained classified copolymer was used as a T cell separating material.

Using the T cell separating material thus obtained, a T cell separating apparatus was prepared in substantially the same manner as in Example 1.

A leukocyte suspension was prepared in substantially the same manner as in Example 1 except that a PBS solution having a bovine serum albumin dissolved therein in a concentration of 5 g/dl was used instead of pure fetal calf serum.

Using the above-obtained separating apparatus, the leukocyte suspension was subjected to substantially the same separating procedures as in Example 1 except that the separating apparatus was washed with a PBS solution having a bovine serum albumin dissolved therein in a concentration of 5 g/dl instead of pure fetal calf serum prior to use.

The collected fraction containing T cells was analyzed in the same manner as in Example 1. The results are shown in Table 1.

COMPARATIVE EXAMPLE 1

Nylon wool of 3 denier was disentangled appropriately by means of a forceps and 0.3 g of the disentangled nylon wool was packed into the cylinder of a polypropylene syringe having a capacity of 5 ml so that the nylon wool was packed uniformly into the cylinder of the syringe to the height of scale reading 2.5 ml. A solution consisting of 5% by volume of fetal calf serum and 95% by volume of PBS was poured into the cylinder of the syringe to the upper end of the packed nylon wool, and the syringe was allowed to stand for 1 hour at room temperature (about 23° C.). Then, 0.5 ml of the same leukocyte suspension as prepared in Example 1 was introduced into the cylinder of the syringe from its top portion and the cylinder was maintained at 37° C. for 1 hour. Then, 10 ml of PBS was supplied to the syringe so that the cells which were not adsorbed on the nylon wool were washed out and the fraction containing the T cells was collected at a flow rate of 2 ml/min. Thus, there was obtained a T cell fraction.

The collected fraction containing T cells was analyzed in the same manner as in Example 1. The results are shown in Table 1.

EXAMPLE 9

The same leukocyte fraction (having a total cell number of $2 \times 10^7$) as prepared in Example 1 was dispersed in 10 ml of a medium RPMI-1640 containing a fetal calf serum having a protein content of 4.3 g/dl in a concentration of 10% by volume. The medium with the leukocyte fraction suspended therein were pipetted into four polystyrene Petri dishes (each having a diameter of 60 mm and a height of 15 mm) which had previously been washed with PBS two times after pure fetal calf serum had been added to the four Petri dishes and they had been allowed to stand overnight. Then, the medium in each Petri dish was allowed to stand in a $CO_2$-incubator, in which the carbon dioxide gas concentration was 5%, at 37° C. for 1 hour. Thus, there was obtained a leukocyte suspension having an increased proportion of T cells to the total cells. The obtained leukocyte suspension was found to have the following proportions of cells; T cell: 74.5%, B cell: 8.2%, monocyte and granulocyte: 5.6%.

Using the separating apparatus as used in Example 2, the leukocyte suspension thus obtained was subjected to the same separation procedures as in Example 1.

The collected fraction containing T cells was analyzed in the same manner as in Example 1. The results are shown in Table 1.

COMPARATIVE EXAMPLE 2

A nylon 66 cord having a diameter of 0.4 mm was cut to obtain pellets each having a 0.4 mm length. After the pellets were immersed in 1 N HCl overnight at room temperature, the pellets were washed sufficiently with PBS.

Using the separating apparatus which was prepared by packing the above-obtained pellets into the column as used in Example 1, the same leukocyte suspension as prepared in Example 1 was subjected to the same separation procedures as in Example 1.

The collected fraction containing T cells was analyzed in the same manner as in Example 1. The results are shown in Table 1.

COMPARATIVE EXAMPLE 3

Using the separating apparatus as used in Comparative Example 2, the same leukocyte suspension as obtained in Example 9 was subjected to substantially the same procedures as in Example 1.

The collected fraction containing T cells was analyzed in the same manner as in Example 1. The results are shown in Table 1.

What is claimed is:

1. A method for separating T cells from leukocytes which comprises contacting an animal serum protein solution having leukocytes suspended therein, said leukocytes comprising T cells and non-T cells, with a hydrophobic, water-insoluble, granular porous organic polymer having an average pore diameter of 500 Å to below 5,000 Å and a total pore volume of 0.1 ml/g to below 4 ml/g, said total pore volume being measured by means of a mercury penetration porosimeter, to adsorb the non-T cells on said porous organic polymer while leaving substantially the T cells unadsorbed, and recovering the T cells left unadsorbed.

2. A method according to claim 1, wherein said porous organic polymer has a grain diameter of $40\mu$ to below $800\mu$.

3. A method according to claim 1, wherein the animal serum protein having leukocytes suspended therein solution contains animal serum protein in a concentration of 1 to 7 g/dl.

4. A method according to claim 3, wherein the animal serum protein is a fetal mammalian serum protein.

5. A method according to claim 1, wherein, before the contacting of the animal serum protein solution having leukocytes suspended therein with the porous polymer said porous polymer is equilibrated with an animal serum protein solution having an animal serum protein concentration of 1 to 7 g/dl.

6. A method according to claim 1, wherein the porous organic polymer has animal serum protein adsorbed thereon and dried.

7. A metod according to claim 6, wherein, before the contacting of the animal serum protein solution having leukocytes suspended therein with the porous polymer, said porous polymer is equilibrated with an animal serum protein solution having an animal serum protein concentration of 0.1 to 7 g/dl.

8. A method according to claim 6, wherein the animal serum protein adsorbed on said porous organic polymer is a fetal mammalian serum protein.

TABLE 1

| | No. | Proportion of T cells to the total cells (%) after separation | Proportion of B cells to the total cells (%) after separation | Proportion of monocyte and granulocyte to the total cells (%) after separation | Survival rate of all the cells (%) after separation | Recovery of T cells (%) |
|---|---|---|---|---|---|---|
| Example | 1 | 89.3 | 2.1 | 2.4 | 99 | 95.6 |
| | 2 | 91.3 | 1.5 | 1.2 | 97 | 90.6 |
| | 3 | 93.4 | 0.7 | 0.2 | 97 | 94.0 |
| | 4 | 93.0 | 0.9 | 0.3 | 98 | 87.7 |
| | 5 | 93.1 | 0.8 | 0.2 | 98 | 89.6 |
| | 6 | 90.8 | 1.2 | 0.8 | 98 | 91.0 |
| | 7 | 88.1 | 0.8 | 1.0 | 96 | 78.5 |
| | 8 | 85.6 | 1.9 | 3.5 | 97 | 89.3 |
| | 9 | 92.3 | 0.7 | 0.8 | 97 | 91.2 |
| Comparative Example | 1 | 85.2 | 3.7 | 2.3 | 96 | 40.2 |
| | 2 | 83.1 | 3.1 | 6.7 | 96 | 88.1 |
| | 3 | 88.2 | 1.6 | 1.2 | 97 | 86.5 |

* * * * *